United States Patent
Hedge et al.

(10) Patent No.: US 6,395,325 B1
(45) Date of Patent: May 28, 2002

(54) POROUS MEMBRANES

(75) Inventors: Anant V. Hedge, Newark; David K. Swanson, Campbell, both of CA (US)

(73) Assignee: SciMed Life Systems, Inc., Maple Grove, MN (US)

( * ) Notice: Subject to any disclaimer, the term of this patent is extended or adjusted under 35 U.S.C. 154(b) by 0 days.

(21) Appl. No.: 09/573,071

(22) Filed: May 16, 2000

(51) Int. Cl.$^7$ .................. A61L 15/00; A61L 27/00; B05D 1/32

(52) U.S. Cl. .................. 427/2.11; 427/407.1; 427/2.24; 427/2.3; 427/2.31; 427/243; 427/244; 427/245; 427/282

(58) Field of Search .............. 427/407.1, 2.24, 427/2.11, 2.3, 2.31, 243, 244, 245, 282

(56) References Cited

U.S. PATENT DOCUMENTS

| | | | | |
|---|---|---|---|---|
| 3,957,941 | A | 5/1976 | Kawaguchi | 264/234 |
| 3,962,258 | A | 6/1976 | Archibald et al. | 260/293.53 |
| 3,980,605 | A | 9/1976 | Steigelmann et al. | 260/30.8 DS |
| 4,113,912 | A | 9/1978 | Okita | 428/290 |
| 4,164,529 | A | 8/1979 | Fujita et al. | 264/565 |
| 4,302,334 | A | 11/1981 | Jakabhazy et al. | 210/500.2 |
| 4,560,599 | A | * 12/1985 | Regen | 428/36 |
| 4,589,964 | A | 5/1986 | Mayhan et al. | 522/85 |
| 4,664,669 | A | 5/1987 | Ohyabu et al. | 623/66 |
| 4,686,267 | A | 8/1987 | Ellis et al. | 526/245 |
| 4,766,189 | A | 8/1988 | Tsuetaki et al. | 526/245 |
| 4,780,411 | A | 10/1988 | Piejko et al. | 422/56 |
| 4,781,978 | A | * 11/1988 | Duan | 428/383 |
| 4,798,847 | A | 1/1989 | Roesink et al. | 521/50 |
| 4,800,082 | A | 1/1989 | Karbowski et al. | 424/409 |
| 4,885,147 | A | 12/1989 | Murakami et al. | 423/261 |
| 4,898,913 | A | 2/1990 | Ziemelis et al. | 525/301 |
| 4,900,449 | A | 2/1990 | Kraus et al. | 210/651 |
| 4,996,275 | A | 2/1991 | Ellis et al. | 526/245 |
| 5,026,781 | A | 6/1991 | Ziemelis et al. | 525/301 |
| 5,084,173 | A | * 1/1992 | Nitadori et al. | 210/321.89 |
| 5,209,849 | A | 5/1993 | Hu et al. | 210/490 |
| RE34,296 | E | 6/1993 | Roesink et al. | 521/50 |
| 5,235,013 | A | 8/1993 | Ito et al. | 526/245 |
| 5,534,150 | A | 7/1996 | Bastioli et al. | 210/640 |
| 5,695,829 | A | 12/1997 | Quiney, III et al. | 427/560 |
| 5,773,488 | A | 6/1998 | Allmér | 522/46 |
| 5,846,421 | A | * 12/1998 | Ohtani | 210/493.2 |
| 5,863,645 | A | * 1/1999 | Misoo et al. | 428/314.2 |
| 5,989,628 | A | * 11/1999 | Haga et al. | 427/164 |

* cited by examiner

Primary Examiner—Fred J. Parker
Assistant Examiner—Jennifer Kolb Michener
(74) Attorney, Agent, or Firm—Lyon & Lyon LLP

(57) ABSTRACT

This invention relates to a novel method for the formation of porous hydrophilic membranes, to the membranes themselves, and to uses for them.

42 Claims, No Drawings

POROUS MEMBRANES

FIELD OF THE INVENTION

The present invention relates generally to the fields of organic chemistry, polymer chemistry, materials science, medicine and medical device technology. More specifically, it relates to a method for producing porous membranes, in particular hydrophilic porous membranes, to the membranes per se and to uses for them.

BACKGROUND OF THE INVENTION

Porous membranes are well-known and have considerable utility. They find use, for instance, in osmosis, reverse osmosis, chromatography, filtration, ion exchange and dialysis. They also are useful as components of medical devices such as stents, catheters and timed-release drug delivery systems.

Presently, porous membranes are made by taking a solution of a polymer or polymers, casting a thin film of the solution on a support base such as a glass plate, allowing partial evaporation of the solvent from the cast film for a pre-determined period of time and then contacting the partially evaporated cast film with a leaching liquid to remove remaining solvent and render the film porous.

When the milieu in which a porous membrane to be used is aqueous, such as in water filtration devices and dialysis, it is desirable that the porous membrane itself be hydrophilic, that is, that it have an affinity for water and be freely wettable. Furthermore, a hydrophilic membrane is preferred when the intended use is in vivo because ion transport occurs much more readily through such a membrane than through a hydrophobic membrane.

It is possible to prepare a hydrophilic membrane by the above-described procedure using one or more polymers which are inherently hydrophilic. However, there are relatively few such polymers known in the art and membranes made from them have limited utility because they lack mechanical strength, chemical resistance and aging and thermal stability. Thus, while polymers such as regenerated cellulose, some polyamides (nylons), polyvinyl alcohols, polyacrylic acid, polyethylene glycol, polyvinylpyrrolidone, polyvinylamine and the like can be formed into hydrophilic membranes, they all lack one or more of these highly desirable characteristics. Heat stability is particularly important in relation to ablation catheters which cause lesions in tissue by heating the tissue where it comes in contact with the catheter tip.

One approach presently employed to overcome the shortcomings of hydrophilic membranes made from hydrophilic polymers is to prepare a membrane using a hydrophobic polymer which results in a membrane having generally superior mechanical strength, heat stability and chemical resistance, and then physically or chemically modifying the membrane surface to render it hydrophilic. Means for accomplishing this include, among others, corona discharge treatment of the membrane surface and the grafting of hydrophilic polymers onto to the surface to render the membrane hydrophilic.

An alternate approach to the above problem is to use a combination of polymers, one or more which is hydrophobic, to give mechanical strength, heat stability and chemical resistance to the resulting membrane and one or more of which is hydrophilic, a sufficient amount of which is included to render the membrane hydrophilic while retaining the beneficial properties conferred by the hydrophobic polymer.

Each of the above techniques suffers from drawbacks which limit their utility. For example, some are expensive, either due to equipment requirements or raw material costs, some require the use of hazardous materials, some are difficult to control with regard to such parameters as degree of cross-linking, leaching of hydrophilic polymer from the membrane, homogeneity of hydrophilicity, control of pore size and the nature of the surfaces to which the membrane can be applied. What is needed is an inexpensive, safe and controllable method for forming porous membranes, in particular, hydrophilic porous membranes that have desirable physical and chemical characteristics and that can be formed on virtually any surface.

SUMMARY

The present invention provides the needed inexpensive, controllable method for forming a porous membrane, in particular a hydrophilic porous membrane which is mechanically strong, chemical resistant, heat stable and which can be formed on virtually any surface.

Thus, one aspect of this invention is a method for forming a porous membrane, comprising: dissolving one or more polymers in one or more solvents at a temperature at which a true solution of the polymer or polymers forms; applying the solution to a surface; and, drying the applied solution at a temperature that is above the flash point of each of the solvents and below the softening point of each of the polymers used until the solvent or solvents have been essentially completely evaporated.

A second aspect of this invention is a method of forming a porous membrane as set forth above using one polymer.

It is an aspect of this invention that the one polymer used is a hydrophobic polymer.

It is an aspect of this invention that the one polymer used is a hydrophilic polymer.

A further aspect of this invention is use of the method set forth above using a plurality of polymers.

A still further aspect of this invention is use of the method set forth above using a plurality of polymers where one or more of the plurality of polymers used is a hydrophobic polymer and one or more of the plurality of polymers used is a hydrophilic polymer.

A presently preferred aspect of this invention is use of the method set forth above in which the porous membrane formed is hydrophilic.

Another aspect of this invention is use of the method set forth above where the hydrophobic polymer or polymers are dissolved in the solvent or solvents before the hydrophilic polymer or polymers are added.

It is a presently preferred aspect of this invention that the hydrophobic polymer or polymers used in the method set forth above each has a softening point above 100° C.

It is likewise a presently preferred embodiment of this invention that the hydrophilic polymer or polymers used in the method set forth above each has a softening point above 100° C.

It is an aspect of this invention that two polymers, one hydrophobic and the other hydrophilic, are used in the method set forth above.

A further presently preferred embodiment if this invention is the use of two polymers in the method set forth above where one of the polymers is poly(vinylidene fluoride), which is hydrophobic, and the other polymer is poly(N-vinylpyrrolidone), which is hydrophilic.

It is an aspect of this invention that, when poly(vinylidene fluoride) and poly(N-vinylpyrrolidone) are used in the method of this invention, the weight/weight ratio of poly (vinylidene fluoride) to poly(N-vinylpyrrolidone) is from about 1:0.5 to about 1:2.

A still further aspect of this invention is that when poly(vinylidene fluoride) and poly(N-vinylpyrrolidone) are used in the method of this invention, the weight/weight ratio of poly(vinylidene fluoride) to poly(N-vinylpyrrolidone) used is about 1:1.

Another aspect of this invention is that, when poly (vinylidene fluoride) and poly(N-vinylpyrrolidone) are used in the method of this invention, the solvent used comprises N, N-dimethylacetamide.

In a presently preferred aspect of this invention that, when poly(vinylidene fluoride) and poly(N-vinylpyrrolidone) are used in the method of this invention, the solvent also contains an acid.

It is an aspect of this invention that, when poly(vinylidene fluoride) and poly(N-vinylpyrrolidone) are used in the method of this invention, the acid used is an organic acid.

It is a presently preferred aspect of this invention that, when poly(vinylidene fluoride) and poly(N-vinylpyrrolidone) are used in the method of this invention, the acid used is glacial acetic acid.

A further aspect of this invention is that, when poly (vinylidene fluoride) and poly(N-vinylpyrrolidone) are used in the method of this invention and the solvent is N,N-dimethylacetamide, the temperature at which the poly (vinylidene fluoride) is dissolved in N,N-dimethylacetamide is from about 30° C. to about 50° C.

In a presently preferred aspect of this invention, when poly(vinylidene fluoride) and poly(N-vinylpyrrolidone) are used and N,N-dimethylacetamide is the solvent, the temperature at which the poly(vinylidene fluoride) is dissolved in the N,N-dimethylacetamide is from about 35° C. to about 40° C.

It is an aspect of this invention that, when poly(vinylidene fluoride) and poly(N-vinylpyrrolidone) are used in the method described above, and N,N-dimethylacetamide is the solvent the temperature at which the poly(N-vinylpyrrolidone) is dissolved in the N,N-dimethylacetamide is about 18° to about 30° C.

A presently preferred embodiment of this invention is that, when N,N-dimethylacetamide used as the solvent in the method described above, the temperature at which they applied solution is dried, which temperature is above the flash point of the solvent, is from about 88° C. to about 92° C.

It is an aspect of this invention that the surface to which the solution of a polymer or polymers is applied in the method described above is a mold.

The mold is a balloon mold in yet another aspect of this invention.

It is an aspect of this invention that the surface to which the solution of a polymer or polymers is applied in the method described above is a medical device.

The above medical device is a diagnostic device in a further aspect of this invention.

The medical device is a therapeutic device in another aspect of this invention.

The therapeutic device is an ablation catheter in a further aspect of this invention.

The therapeutic device is a drug delivery device in yet another aspect of this invention.

The drug delivery device is an electrophoretic drug delivery device in an aspect of this invention.

A hydrophobic porous membrane made using one or more hydrophobic polymers in the method described above is an aspect of this invention.

A hydrophilic porous membrane made using one or more hydrophilic polymers is likewise an aspect of this invention.

A hydrophilic porous membrane made using two polymers one of which is poly(vinylidene fluoride), which is hydrophobic, and the other of which is poly(N-vinylpyrrolidone), which is hydrophilic, in the method described above is an aspect of this invention.

A biocompatible hydrophilic porous membrane made using the method of described above is also an aspect of this invention.

The porous membrane formed has a thickness of from about 0.05 to about 50 mils in another aspect of this invention.

In a presently preferred embodiment of this invention the porous membrane formed has a thickness of from about 1 to about 5 mils.

It is an aspect of this invention that the porous membrane formed by the method herein has pores that are from about 0.0001 to about 10.0 microns in diameter.

An aspect of this invention is a method for forming a selectively porous membrane, comprising:

dissolving one or more first polymers in one or more first solvents at a temperature at which a true solution of the polymer or polymers forms to give a first solution;

applying the first solution to a surface;

drying the applied solution at a temperature that is above the flash point of the solvent or each of the solvents and below the softening point of the polymer or each of the polymers until the solvent or solvents have been substantially completely evaporated to give a first membrane;

masking the first membrane to protect those areas in which porosity is to be maintained;

dissolving one or more second polymers in one or more second solvents at a temperature at which a true solution of the polymer or polymers forms to give a second solution;

applying the second solution to the masked membrane;

drying the applied second solution at a temperature that is below the flash point of the second solvent or solvents and below the softening point of the second polymer or polymers until the second solvent or solvents have been substantially completely evaporated, to give a second membrane; and, removing the mask.

It is an aspect of this invention that, in the method immediately above, the first solution and the second solution are the same solution.

It is also an aspect of this invention that, in the above method, the first and second membranes are both hydrophilic.

In a further aspect of this invention, one of the membranes formed by the above method is hydrophobic and one of the membranes formed is hydrophilic.

It is an aspect of this invention that the first, porous membrane is hydrophilic and the second, non-porous membrane is hydrophobic.

Finally, it is an aspect of this invention that the first, porous membrane is hydrophobic and the second, non-porous membrane is hydrophilic.

DETAILED DESCRIPTION

As used herein, the term "about" means ±15%.

"Substantially" as used herein, means 90–100%, preferably 95–100%, most preferably 98–100%.

As used herein, the term "porous" or "porosity" refers to having a plurality of channels through a membrane such that materials smaller in diameter than the channel can move through the membrane by way of the channels. Pores of any useful size may be formed using the method of this invention. Thus, the pores may have diameters in the range of about 0.0001 to about 0.1 microns in diameter, which, for the purposes of this invention, are referred to as micropores, the membrane then being "microporous," from about 0.1 to about 10 microns, which, for the purposes of this invention, are be referred to as mini pores, the membrane then being "miniporous," or greater than 10 microns, which, for the purposes of this invention, are referred to as macropores and the resulting membrane "macroporous." Preferably, the pores are micropores in the range of about 0.01 to about 0.025 microns in diameter and the membrane is microporous.

A "membrane," as used herein, refers to a thin, pliable layer of material which formed by applying a solution containing a polymer or mixture of polymers to a surface and then removing the solvent. When the solvent is removed the thin layer of material remains. The layer of material may be removed from the surface and function as a stand-alone structure or it can remain on the surface on which it was formed as a permanent coating such as, without limitation, a membrane coating on the surface of a medical device like a catheter. Membranes of this invention may have a thickness of from about 0.5 to about 50 mils, preferably from 0.75 to about 20 mils, most preferably from about 1 to about 5 mils.

By "dissolving," as used herein, is meant mixing a solid or solids with a liquid such that a true solution of the solid or solids in the liquid is formed.

By "applying" a solution to a surface, as used herein, is meant placing a layer of the solution on the surface by such techniques as, without limitation, dipping the surface into and then withdrawing it from the solution such that a layer of the solution adheres to the surface, brushing the solution onto the surface and spraying the solution onto the surface.

As used herein, a polymer refers to a large molecule made of many small repeating units, called monomers. Polymers consisting of one kind of repeating unit are called homopolymers and have the structure -A-A-A-A-A-A-A- wherein A is a monomer. Polymers consisting of two or more different repeating units, e.g., A, B and C, are called copolymers. Copolymers may be random (e.g., -A-B-A-C-B-A-C-B-, etc), alternating, (e.g. -A-B-C-A-B-C-, etc), or block (-A-A-B-B-B-A-A-A-C-C-A-A-, etc). Polymers may also be linear, i.e., long chains of monomers, they may be branched, in which side chains are attached to the long chains, or they may be cross-linked, wherein two or more chains are joined together by side chains. The degree of polymerization, that is, the average number of repeating units in a chain, is usually represented by the molecular weight of the polymer. Thus, if a repeating unit has a molecular weight of, for example, 60, and a chain of those repeating unit has a molecular weight of 60,000, then there are, on the average, 1000 repeating units in each polymer chain. The polymers used in the method of this invention have molecular weights of from about 10,000 to about 1,000,000, preferably from about 10,000 to about 500,000, most preferably from about 20,000 to about 200,000.

As used herein, a "true solution" refers to a uniform, homogenous mixture of components in which the major component is called the solvent and the minor component is called the solute. When liquids and solids are used to form a solution, the liquids are the solvents and the solids are the solutes. The solutes in a true solution are of molecular size and the solution appears homogenous under a microscope. The solutes in a true solution cannot be separated from the solvents by filtration.

The "flash point" of a liquid is the lowest temperature at which the liquid gives off sufficient vapor to form an ignitable mixture with air near the liquid surface when exposed to a spark or open flame. The flash points of many solvents are available from sources such as Material Safety Data Sheets (MSDSs) and the like. If the flash point of a particular solvent is not known, it can be determined by a closed cup procedure such as the Tagliabue (Tag) or Set-a-Flash methods, which are well-known in the art.

The "softening point" of a polymer is the temperature at which a sample of the polymer, becomes soft, deformable and capable of flow. Numerous procedures for determining the softening point of a polymer are known in the art such as, without limitation, the Vicat test, the deflection temperature or heat distortion test, the polymer melt or stick temperature test and the zero strength temperature test. The softening point (and the method used to determine it) of many polymers can be found in the literature. If unavailable, any of the preceding procedures may be employed to determine the softening point of a polymer intended for use in the method described herein.

As used herein, a "hydrophobic" polymer refers to a polymer which has little affinity for water or aqueous solutions, is water-repellant and, in bulk form, absorbs less than about 0.5% of its weight in water over a 24 hour period or 4% or less at equilibrium as measured by ASTM D570.

A "hydrophilic" polymer, as used herein, refers to a polymer which has an affinity for water, is freely wettable and absorbs more than 0.5% of its weight in water over 24 hours or more than 4% at equilibrium as measured by ASTM D570.

As used herein, "poly(vinylidene fluoride)" refers to a polymer having the repeating unit:

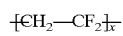

As used herein, "poly(N-vinylpyrrolidone) refers to a polymer having the repeating unit:

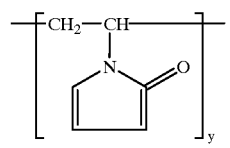

The term "biocompatible" or "biocompatibility," as used herein, refers to a material, not normally found in the body, which, when invasively placed in the body, does not have a deleteriously effect, such as toxicity, thrombogenicity, immune system activation and the like.

An "acid," as used herein, refers to a hydrogen-containing substance that dissociates on solution in water to produce one or more hydrogen ions. Acetic acid is an organic acid having the chemical formula $CH_3COOH$. Glacial acetic acid is acetic acid which contains no more than 0.2% by weight water.

A "mold," as used herein refers, to a form of any shape to which a solution of a membrane-forming polymer or polymers can be applied such as, without limitation, a flat sheet, a mandrel, or a balloon. A "balloon mold" refers to mold which assumes a desired shape on inflation with a gas or a liquid and to which a solution of a membrane-forming polymer can be applied, the mold then being deflated to remove the membrane. A balloon mold can be of any desired shape such as, without limitation, a spherical balloon mold, an elongated balloon mold, a fluted balloon mold and the like.

A "mask," as used herein, refers to a removable coating which can be applied to a surface on which a porous membrane has been formed by the method described herein. The purpose of the coating is to protect selected areas of the porous membrane during the formation of a second non-porous membrane on top of the porous membrane. When the second membrane has fully formed, the mask is stripped from the surface taking with it any of the non-porous membrane adhered to it. This leaves a membrane which is porous in the areas that were protected by the mask and non-porous in the areas the mask did not cover.

Hydrophobic polymers useful in the method of this invention and as components of hydrophobic microporous membranes produced by the method include, without limitation, polystyrene, polycarbonate, polyacrylates, polymethacrylates, polyetherimides, polyamides, polyimides, polysulfones, polyethersulfones, various fluorocarbon resins such as, again without limitation, poly(vinyl fluoride), poly(vinylidene fluoride), poly(tetrafluoroethylene), poly(trifluorochloroethylene) and the like. In addition, copolymers of these and other hydrophobic polymers can be used.

Poly(vinylidene fluoride) is a presently preferred hydrophobic polymer to be used in the method described herein and as a component of a hydrophilic microporous membrane made by the method.

Hydrophilic polymers useful in the method of this invention as components of hydrophilic microporous membrane produced by the method include, without limitation, poly(vinyl alcohol), poly(ethylene oxide), poly(ethylene glycol), poly(hydroxyethyl methacrylate), poly(acrylic acid), poly(N-vinylpyrrolidone), poly(N-vinyl-2-pyrrolidone), poly(vinyl pyridine), poly(acrylonitrile), poly(carboxylic acids), aromatic polyamides, poly(sulfonates).

A presently preferred hydrophilic polymer to use in the method of this invention and as a component of a hydrophilic microporous membrane made by the method, is poly(N-vinylpyrrolidone).

It is particularly important that the solvent selected be one which is capable of forming true solutions of each of the polymers used in the method of this invention. While any solvent which achieves this end may be used, polar aprotic solvents are particularly suitable. Thus, solvents useful in the method of this invention include, without limitation, acetone, tetrahydrofuran, dioxane, pyridine, N-methylpiperidine, dimethylsulfoxide, N-methylmorpholine, N-methylpyrrolidone, N,N-dimethyformamide, N,N-dimethylacetamide and the like.

A presently preferred solvent to use in the method of this invention is N,N-dimethylacetamide.

Other hydrophobic or hydrophilic polymers and other solvents which can be used to prepare a hydrophobic microporous or hydrophilic microporous membrane using the method described above will be apparent to those skilled in the art based on the disclosures herein. Such other polymers and solvents are within the scope of this invention.

The temperature at which the solvent is maintained during the dissolution of the polymer or polymers is likewise an important aspect of this invention. The temperature should be selected such that each of the polymers used will form a true solution in the selected solvent. It is well understood in the art that polymers have a lower critical solution temperature (LCST) and an upper critical solution temperature (UCST). On heating, as the temperature of a solvent approaches the LCST, the solvent becomes thermodynamically poorer and poorer until, at or above the LCST, phase separation occurs and the polymer is no longer soluble in the solvent. Likewise, on cooling, when the temperature of a solvent approaches the UCST, it becomes a thermodynamically poorer and poorer solvent until, at or below the UCST, phase separation occurs and the polymer is once again no longer soluble in the solvent. Thus the temperature selected for the dissolution of the polymer or polymers used in the method of this invention must be below the LCST and above the UCST of each polymer being used in the selected solvent. The LCST and UCST of polymers can, in some instances, simply be looked up in the appropriate polymer literature. In any event, the LCST and UCST of any polymer in any solvent can be readily determined, without undue experimentation, using procedures well known in the art. Thus, an appropriate temperature for dissolving any combination of polymers in any solvent for use in the method of this invention can be easily ascertained based on the disclosures herein.

In a presently preferred embodiment of this invention, when the polymers used are poly(vinylidene fluoride) and poly(N-vinylpyrrolidone) and the solvent is N,N-dimethylacetamide, the temperature at which the poly(vinylidene fluoride) is dissolved is from about 25° C. to about 50° C., preferably from about 35° C. to about 40° C.

The temperature at which the poly(N-vinylpyrrolidone) is dissolved in the N,N-dimethylacetamide is from about 18° to about 22° C. in a presently preferred embodiment of this invention.

When a plurality of polymers is used in the method of this invention, the solution of those polymers may be unstable and prone to gel formation. This can be prevented by keeping the solution acidic, that is, at a pH of from about 2.0 to about 6.0. Any acid, inorganic or organic, which will create the desired pH solution and which does not itself react with any of the polymers or the solvent, may be used. Presently preferred acids are relatively weak organic acids such as acetic acid.

Another aspect of this invention is that, when N,N-dimethylacetamide used as the solvent in the method described above, the temperature which is above the flash point of the solvent is from about 77° C. to about 95° C.

Another aspect of this invention is that, when N,N-dimethylacetamide used as the solvent in the method described above, the temperature which is above the flash point of the solvent is from about 77° C. to about 95° C.

Once a true solution of the polymer of polymers has been achieved, the solution can be applied to a surface to form a microporous membrane. Any surface of any desired conformation can be used. For example, without limitation, the solution can be applied to the exterior surface of a mold to which the resulting membrane will not stick and the membrane, after drying, can be removed from the surface to give a microporous membrane in the shape of that surface. Or the solution can be applied to the inner surface of a mold having a closed configuration (such as an injection mold or the like) and, after drying, the mold can be opened to give a microporous membrane in the shape of the mold. In another, presently preferred embodiment, the mold is a collapsible balloon, again of any desired shape. The balloon can be inflated, coated with the solution and then dried in an oven at an appropriate temperature. The balloon is then deflated and removed leaving a microporous membrane in the shape of the inflated balloon.

Alternatively, a balloon mold can be "inflated" using a liquid which is maintained at an appropriate drying temperature and the solution of the polymer or polymers is applied to the heated balloon. As above, once drying is completed, the liquid is removed from the balloon mold which is then collapsed and can be withdrawn from the shaped microporous membrane.

The drying temperature of the solution-coated surface is critical; it must be above the flash point of the solvent, or each of a combination of solvents, used and below the softening point of the polymer or each of a plurality of polymers used. Without being bound to any particular theory, it is the removal of the solvent at a temperature above the flash point of the solvent or solvents which results in the formation of the pores.

The porous membranes of this invention will be useful in any application where such membranes are presently used, such as, without limitation, normal filtration, ultrafiltration, chromatography, osmosis, reverse osmosis, fabric coating, dialysis, and the like. With regard to hydrophilic microporous membranes produced by the method described herein, a presently preferred use is in medical devices, such as catheters, for example as guide wire coatings, and, in particular, ablation catheters as components of the ablation energy generating structure.

Ablation catheters are used to create tissue lesions in the region of the heart as a method of treating cardiac arrhythmias. Ablation is achieved by transmitting heat-creating electrical energy to the site to be ablated. Electrical energy is delivered to the site to be ablated by minute electrodes. In some configurations of ablation catheters, the electrodes are metal strips having a generally rectangular cross-section. A problem can occur with such electrodes in that an edge current, that is, and undesirable current concentration, can arise at the edges of the electrode. This can result in "hot spots" in the electrode, which, in turn can result in excessive damage to tissue in contact with the electrode. Coating the electrodes with a hydrophilic porous membrane, which will reduce the discontinuity in conductivity between the electrode and the surrounding tissue because it has a resistivity similar to that of the tissue, can alleviate or even eliminate edge currents.

By selecting the appropriate polymers for the formation of a hydrophilic membrane depending on the environment to which the membrane will be exposed, which can be accomplished without undue experimentation by those skilled in the art based on the disclosure herein, using the hydrophilic porous membranes of this invention as coatings for electrodes to reduce or eliminate edge current will be applicable to any type of electrode in any type of application where edge current is a problem.

In another ablation catheter assembly construct, the electrodes comprise a microporous electrode assembly. This assembly is a pliable membrane which, when at the desired location within a patient, can be inflated with an electrically-conductive medium containing ions. The medium is connected to a source of electrical energy. The micropores of the membrane are of such a size as to permit ions to freely pass through the membrane while allowing substantially no liquid perfusion. Thus, the membrane enables ionic transport of electrical energy through the membrane to the exterior surface of the membrane and thence to the tissue to be ablated. Examples of this type of ablation catheter assembly can be found in U.S. Pat. Nos. 5,961,513 and 5,840,076, which are incorporated by reference, including any drawings, as if fully set forth herein.

Another ablation catheter design uses an electrode, the structure of which comprises an expandable-collapsible mesh. The mesh can be constructed so as to assume virtually any shape when expanded thus permitting deliver of ablation energy in any desired pattern. The mesh electrode is separated from the tissue to be ablated by a microporous conductive shell which likewise is expandable-collapsible (U.S. Pat. No. 5,891,136, which is incorporated by reference, including any drawings, as if fully set forth herein).

Co-pending application Ser. No. 08/984,414, which is likewise incorporated by reference, including any drawings, as if fully set forth herein, provides yet another catheter design which incorporates flexible microporous membranes.

It is generally preferred that the membranes used in the design of catheters such as those indicated above be hydrophilic for the reasons discussed elsewhere herein, that is, greater enablement of ionic transport through the membrane. A presently preferred polymer for the formation of such hydrophilic membranes is regenerated cellulose. However regenerated cellulose suffers from a lack of mechanical strength, chemical resistance and aging and heat stability, which could result in failure of the membrane while in use. A hydrophilic microporous membrane made by the method of this invention and having superior mechanical strength, chemical resistance and aging and heat stability, could be advantageously substituted for regenerated cellulose in the above-described catheters.

In another catheter design in which hydrophilic microporous membranes prepared by the method of this invention could find substantial use is one in which, rather than wire or mesh electrodes, the ablation energy is delivered by means of imprinted circuitry, either on the surface of a non-compliant electrode assembly or on the surface of an expandable-collapsible membrane electrode. A membrane of this invention could be coated over the imprint of a non-compliant electrode assembly as a protective barrier between the imprinting material and the patient. Or, when an expandable-collapsible electrode membrane is used, a membrane of this invention could be formed as an expandable-collapsible outer membrane, likewise employed as a protective layer between the electrode assembly and the patient.

A further catheter design to which the mechanically strong hydrophilic microporous membranes of this invention could be advantageously applied would be a design wherein the electrode pattern desired is imprinted directly on the interior surface of a membrane of this invention such that, when the membrane is expanded at the location to be ablated, ablation energy could be controllably delivered to the adjacent tissue.

The membranes of this invention should also find use in drug delivery devices. An example of such a device is a Wolinsky perforated balloon catheter. The device comprises a standard angioplasty catheter having a perforated balloon at the distal end. The catheter is filled with a therapeutic solution and positioned at the site of interest using standard techniques. The balloon is then pressurized which causes the therapeutic agent to push through the balloon and into the adjacent tissue.

A problem with the Wolinsky device is that the holes through which the therapeutic solution exit the balloon are laser drilled and therefore relatively large. Thus, the solution is driven into the tissue as a jet of liquid which, in some instances, can damage the tissue. A proposed solution to this is to use a microporous membrane that would slow the exit of the therapeutic solution due to smaller pore size which would result in the solution "oozing," rather than spraying, through the membrane and into the tissue. Microporous membranes formed by the method described herein should find wide applicability in devices of this type.

The hydrophilic microporous membranes of this invention should also find particular use in electophoretic drug delivery systems. In such systems, a low-level electrical current is applied to drive a therapeutic agent through the membrane into the adjacent tissue. That is, a therapeutic solution is placed in a balloon at the distil end of a catheter. The solution is in contact with a source of electrical energy. When the balloon is in place at the site of interest, it is inflated with a re-circulating infusate of the therapeutic agent. Then, a small electric field is generated between the balloon (the cathode) and a skin patch (the anode). The therapeutic agent then migrates through the membrane under the influence of the electromotive force created.

Other types of balloon-based drug delivery systems in which the porous membranes of this invention should be useful, such as, without limitation, transport/balloon-in-a-balloon delivery systems, infusion sleeves, dispatch catheter coiled balloons delivery systems (*Peripheral Endovascular Interventions,* 1996, White and Fogarty, editors, Mosby, St. Louis, Chapter 29, pp.478–488) will become apparent to those skilled in the art based on the disclosures herein. Use of microporous membranes formed by the method described herein in such applications are within the scope of this invention.

EXAMPLES

The following examples are provided for the purpose of illustration only and are not to be construed as limiting the scope of this invention in any manner whatsoever.

Solution Preparation

Bulk poly(vinylidene fluoride) (PVDF) was dried at 80° to 100° C. for 1 hour before use. Bulk poly(N-vinylpyrrolidone) was kept in a dessicator prior to use. Spectrograde N,N-dimethylacetamide, which was indicated to have a flash point of 77° C., was heated to 35° C. Vigorous stirring of the solvent was begun and PVDF was added until a 25% w/w, PVDF to N,N-dimethylacetamide, solution was achieved. The dissolution process is exothermic so, depending on scale, cooling of the solution may be needed during the addition the PVDF. Once the PVDF is in solution, the solution is allowed to cool to room temperature (about 18°–20° C.). The solution is clear and has a pale yellow color. At this point, while maintaining vigorous stirring, glacial acetic acid was added until the solution was sufficiently acidic to prevent gelling. While continuing the vigorous stirring, bulk poly(N-vinylpyrrolidone) (PVP) was slowly added to the acidic PVDF solution at room temperature. PVP was added until a 25% w/w, PVP to N,N-dimethylacetamide, solution was obtained. When all the PVP was added, stirring was continued for an additional 15 minutes. Stirring was then stopped and the solution allowed to sit for 3–4 at room temperature to allow the PVP to dissolve completely.

Membrane Formation

A poly(tetrafluoroethylene) (TEFLON®) coated stainless steel mandrel was dipped into 15A liquid silicone and dried at ambient temperature for 15 minutes, 50° C. for 30 minutes and then 150° C. for 30 minutes. The mandrel was then cooled to room temperature and the silicone balloon was removed from the mandrel.

The silicone balloon was then mounted on a smaller mandrel which fits inside the balloon and secured to the mandrel with a clip.

The silicone balloon was then inflated and dipped in the solution of PVDF/PVP described above. The coated balloon was immediately placed in an oven, which had been preheated to 90° C., and left there for 20 minutes. The balloon was removed from the oven and allowed to cool to room temperature. The silicon balloon was then collapsed and withdrawn leaving a balloon-shaped hydrophilic microporous membrane.

The thickness of the membrane formed can be varied by controlling the viscosity of the PVDF/PVP solution which, in turn, can be adjusted by varying the w/w percentage of the polymers in the solvent. Alternatively, if a thicker membrane is desired, the mold can be dipped in the PVDF/PVP solution, with drying cycles between dippings, as many times as desired.

The balloon mold used in the above procedure need not, of course, be limited to silicone. Any material can be used that will not stick to the membrane formed or will not react with the polymers or the solvent in which they are dissolved. Furthermore, the balloon material must be capable of withstanding a drying temperature above the flash point of the solvent used.

Selectively Porous Membranes

It is possible, using the method described here, to create membranes that are selectively porous, that is, which are porous in some areas and non-porous in other areas. This can be achieved using the method described herein as follows:

Once a porous membrane has been formed on a surface using the method described herein, a removable mask, in a pattern corresponding to the areas of the membrane where porosity is to be maintained, is applied to the porous membrane. A second solution of a polymer or polymers is then applied to the masked membrane. The polymer or polymers may be the same or different from those used to form the porous membrane. The second solution is dried at a temperature below the flash point of each of the solvent or solvents used to make the second solution. Keeping the drying temperature below the flash point of the solvents results in the formation of a non-porous membrane. Once the non-porous membrane is dry, the mask is removed and with it the non-porous membrane wherever it formed over the mask. What is left is a membrane which is porous where it was protected by the mask and non-porous where it was not protected by the mask during the application and drying of the second solution.

If the same solution of the same polymer or polymers used to form the hydrophilic porous membrane is used as the second solution, the result will be a completely hydrophilic membrane which is porous is some areas and non-porous in others.

It may be desirable to have a selectively porous membrane in which the non-porous regions are hydrophobic rather than hydrophilic. This can be readily accomplished by applying a second solution of a hydrophobic polymer to the masked hydrophilic porous membrane. The second solution is dried at a temperature below the flash point of the solvent or solvents used resulting in the formation of a hydrophobic, non-porous membrane. When the mask is removed, a membrane which is porous and hydrophilic in the areas protected by the mask and non-porous and hydrophobic in the areas not protected by the mask is obtained. In the above example where poly(vinylidene fluoride) is used as the hydrophobic component of the solution and poly(N-vinylpyrrolidone) is used as the hydrophilic component, the second solution would be comprised of poly(vinylidene fluoride) alone. It is, of course, possible to use a solution of a hydrophobic polymer different from that used in the initial solution.

Generally, when forming a selectively porous membrane, it is preferred to form the non-porous membrane using the same polymer or polymers used to form the porous membrane, with the only difference being the drying temperature. Using the same polymer or polymers has the advantage of forming a porous/non-porous membrane in which the two layers have the same physical characteristics, such as expansion rate, toughness and wear. This results in a two-ply membrane having better mechanical integrity and biocompatibility than would be obtained if different polymers, having different physical characteristics, are used to create the porous and non-porous regions of the membrane.

Of course, a selectively porous membrane in which the porous areas are hydrophobic and the non-porous areas are hydrophilic can also be formed by simply reversing the above procedure. That is, a first solution of the hydrophobic polymer or polymers alone is applied and dried at a temperature above the flash point of the solvent or solvents to afford a hydrophobic, porous membrane. A second solution of a hydrophilic polymer or polymers is the applied and dried below the flash point of the solvent or solvents used, resulting in a non-porous hydrophilic membrane.

Additional embodiments of this invention are contained in the claims which follow.

What is claimed:

1. A method for forming a porous membrane, comprising:
   dissolving one or more polymers in one or more solvents at a temperature at which a true solution of the polymer or polymers forms;
   applying the solution to a surface; and,
   drying the applied solution at a temperature that is above the flash point of the solvent or each of the solvents and below the softening point of the polymer or each of the polymers until the solvent or solvents have been substantially completely removed.

2. The method of claim 1 using one polymer.

3. The method of claim 2, wherein the polymer used is a hydrophobic polymer.

4. The method of claim 2, wherein the polymer used is a hydrophilic polymer.

5. The method of claim 1, using a plurality of polymers.

6. The method of claim 5, wherein one or more of the plurality of polymers used is hydrophobic and one or more of the plurality of polymers used is hydrophilic.

7. The method of claim 6, wherein the porous membrane formed is a hydrophilic porous membrane.

8. The method of claim 5, wherein the hydrophobic polymer or polymers are dissolved in the solvent or solvents before the hydrophilic polymer or polymers are added to the solvent or solvents.

9. The method of claim 6, wherein the hydrophobic polymer or polymers each has a softening point above 100° C.

10. The method of claim 9, wherein the hydrophilic polymer or polymers each has a softening point above 100° C.

11. The method of claim 5, wherein two polymers, one hydrophobic and the other hydrophilic, are used.

12. The method of claim 10, wherein:
    the hydrophobic polymer used is poly(vinylidene fluoride); and,
    the hydrophilic polymer used is poly(N-vinylpyrrolidone).

13. The method of claim 12, wherein the weight/weight ratio of poly(vinylidene fluoride) used to poly(N-vinylpyrrolidone) used is from about 1:0.5 to about 1:2.

14. The method of claim 12, wherein the weight/weight ratio of poly(vinylidene fluoride) used to poly(N-vinylpyrrolidone) used is about 1:1.

15. The method of claim 12, wherein the solvent comprises N,N-dimethylacetamide.

16. The method of claim 15, wherein the solvent further comprises an acid.

17. The method of claim 16, wherein the acid is an organic acid.

18. The method of claim 17, wherein the acid is glacial acetic acid.

19. The method of claim 15, wherein the temperature at which the poly(vinylidene fluoride) is dissolved in N,N-dimethylacetamide is from about 30° C. to about 50° C.

20. The method of claim 15, wherein the temperature at which the poly(vinylidene fluoride) is dissolved in the N,N-dimethylacetamide is from about 35° C. to about 40° C.

21. The method of claim 15, wherein the temperature at which the poly(N-vinylpyrrolidone) is dissolved in the N,N-dimethylacetamide is about 18° to about 30° C.

22. The method of claim 12, wherein the temperature which is above the flash point of the solvent is from about 88° C. to about 92° C.

23. The method of any one of claims 1, 5, 11 or 12, wherein the surface to which the solution of the polymer or polymers is applied is a mold.

24. The method of claim 23, wherein the mold is a balloon mold.

25. The method of any one of claims 1, 5, 11 or 12, wherein the surface to which the solution of the polymer or polymers is applied is a medical device.

26. The method of claim 25, wherein the medical device comprises a diagnostic device.

27. The method of claim 25, wherein the medical device comprises a therapeutic device.

28. The method of claim 27, wherein the therapeutic device is an ablation catheter.

29. The method of claim 25, wherein the medical device comprises a drug delivery device.

30. The method of claim 29, wherein the drug delivery device comprises an electrophoretic drug delivery device.

31. A hydrophobic porous membrane made using the method of any one of claims 1, 3 or 5.

32. A hydrophilic porous membrane made using the method of any one of claims 1, 4, 6 or 11.

33. A hydrophilic porous membrane made using the method of any one of claims 12, 13 or 14.

34. A biocompatible hydrophilic porous membrane made using the method of any one of claims 1, 4, 6, 11, 12, 13 or 14.

35. The method of claim 1, wherein the porous membrane formed has a thickness of from about 0.05 to about 50 mils.

36. The method of claim 1, wherein the porous membrane formed has a thickness of from about 1 to about 5 mils.

37. A method for forming a selectively porous membrane, comprising:
    dissolving one or more first polymers in one or more first solvents at a temperature at which a true solution of the first polymer or polymers forms to obtain a first solution;
    applying the first solution to a surface;
    drying the applied solution at a temperature that is above the flash point of the solvent or each of the solvents and below the softening point of the polymer or each of the polymers until the solvent or solvents have been substantially completely removed to form a porous membrane;
    masking the porous membrane to protect those areas in which porosity is to be maintained;
    dissolving one or more second polymers in one or more second solvents at a temperature at which a true solution of the second polymer or polymers forms to give a second solution;

applying the second solution to the masked membrane;

drying the applied second solution at a temperature that is below the flash point of the second solvent or each of the solvents and below the softening point of the second polymer or each of the polymers until the second solvent or solvent have been substantially completely removed to form a non-porous membrane over those portions of the porous membrane where porosity is not to be maintained; and, removing the mask.

38. The method of claim 37, wherein the first and second solutions are the same.

39. The method of claim 38, wherein the first and second membranes formed are both hydrophilic.

40. The method of claim 37, wherein the first and second solutions are different.

41. The method of claim 40, wherein drying the first solution results in formation of a porous, hydrophilic membrane and drying the second solution results in formation of a non-porous, hydrophobic membrane.

42. The method of claim 40, wherein drying the first solution results in formation of a porous, hydrophobic membrane and drying the second solution results in formation of a non-porous, hydrophilic membrane.

* * * * *